(12) United States Patent
Ballard

(10) Patent No.: US 6,187,293 B1
(45) Date of Patent: Feb. 13, 2001

(54) PROCESS FOR MAKING TOOTHPASTE USING LOW LEVELS OF CARRAGEENAN

(75) Inventor: Arthur D. Ballard, Friendship, ME (US)

(73) Assignee: FMC Corporation, Philadelphia, PA (US)

(*) Notice: Under 35 U.S.C. 154(b), the term of this patent shall be extended for 0 days.

(21) Appl. No.: 09/300,248

(22) Filed: Apr. 27, 1999

Related U.S. Application Data

(60) Provisional application No. 60/083,116, filed on Apr. 27, 1998.

(51) Int. Cl.$^7$ .................................................. A61K 7/16
(52) U.S. Cl. ............................................................. 424/49
(58) Field of Search ............................................ 424/49–58

(56) References Cited

U.S. PATENT DOCUMENTS

| | | | |
|---|---|---|---|
| 2,431,622 | * | 11/1947 | Stehrs . |
| 2,431,623 | * | 11/1947 | Siehrs . |
| 2,485,660 | * | 10/1949 | Robertson . |
| 2,751,328 | * | 6/1956 | Sanders . |
| 3,469,996 | * | 9/1969 | Endres et al. . |
| 3,658,556 | * | 4/1972 | Klein et al. ............................. 99/131 |
| 3,956,173 | * | 5/1976 | Towle . |
| 3,962,482 | * | 6/1976 | Comer et al. . |
| 4,029,760 | * | 6/1977 | De Roeck . |
| 4,096,327 | * | 6/1978 | Guiseley . |
| 4,140,757 | * | 2/1979 | Wason et al. . |
| 4,353,890 | * | 10/1982 | Scott ...................................... 424/49 |
| 4,444,747 | * | 4/1984 | Hayes et al. . |
| 4,457,908 | * | 7/1984 | Scott ...................................... 424/49 |
| 4,473,988 | * | 10/1984 | Scott ...................................... 424/49 |
| 4,474,818 | * | 10/1984 | Scott ...................................... 424/49 |
| 4,482,531 | * | 11/1984 | Hayes et al. . |
| 4,529,584 | * | 7/1985 | Mulvey et al. .......................... 424/49 |
| 4,604,280 | * | 8/1986 | Scott ...................................... 424/49 |
| 4,623,552 | * | 11/1986 | Rapp ...................................... 426/575 |
| 4,814,160 | * | 3/1989 | Carter et al. ........................... 424/49 |
| 5,599,527 | * | 2/1997 | Hsu et al. ............................... 424/49 |
| 5,698,182 | * | 12/1997 | Prencipe et al. ........................ 424/49 |
| 5,730,959 | * | 3/1998 | Prencipe et al. ........................ 424/49 |
| 5,788,951 | * | 8/1998 | Blake-Haskins et al. .............. 424/49 |
| 5,843,406 | * | 12/1998 | Mordarski et al. .................... 424/49 |

\* cited by examiner

*Primary Examiner*—Shep K. Rose
(74) *Attorney, Agent, or Firm*—Bruce M. Monroe; Patrick C. Baker; Robert L. Andersen

(57) ABSTRACT

This invention pertains to a process for increasing by at least about 100% the viscosity of a carrageenan-containing dentifrice composition that comprises allowing the composition to quiescently cool from a temperature at or above about 45° C. The process may be applied to making toothpastes having suitable viscosity using carrageenan levels as low as about 0.05 weight percent. The dentifrice compositions are comprised of one or more of the following carrageenans: iota, modified kappa, or mixtures thereof. Toothpastes prepared using this method are easier to process and require much less carrageenan relative to similar viscosity toothpastes prepared by previous methods. This invention also pertains to certain toothpaste compositions having low levels of carrageenan including those made according to this process.

23 Claims, 2 Drawing Sheets

Viscosity Relationship to Temperature and Carrageenan Concentration

FIGURE 1. CONTINUOUS PROCESS

Viscosity Relationship to Temperature and Carrageenan Concentration

PROCESS FOR MAKING TOOTHPASTE USING LOW LEVELS OF CARRAGEENAN

This application claims benefit to U.S. provisional application Ser. No. 60/083,116, filed Apr. 27, 1998.

This invention pertains to a process for making toothpastes using low levels of certain types of carrageenan. More particularly this invention pertains to a process for making toothpaste whereby a toothpaste formulation comprising at least 0.05% by weight of carrageenan is allowed to quiescently cool from a temperature at or above about 45° C. to provide a toothpaste having a Cuban value in the range of about 3 to 12. Carrageenans that may be used include iota, modified kappa, and mixtures thereof. Toothpastes prepared using this method require much less carrageenan relative to similar viscosity toothpastes prepared by previous methods. This invention also pertains to certain toothpaste compositions having low levels of carrageenan including those made according to this process.

BACKGROUND OF THE INVENTION

Many carrageenan-containing toothpastes are generally recognized as having very good properties such as acceptable physical stability, low stringiness and good rheology. Toothpastes with acceptable physical stability do not readily harden on the shelf and do not exhibit phase separation such as water or flavor separation. Low stringiness is important not only to the consumer but also in high volume manufacturing where high speed filling lines require that the toothpaste ribbon cuts off sharply from the tube. Toothpastes having good rheology will be easy to dispense from the tube yet stand up well on the brush. Moreover, these properties may be provided in a carrageenan-containing toothpaste that has appealing taste, has good cleansing effect, is easy to rinse, has excellent mouth feel, and has a smooth, pleasant appearance.

However, despite the well-known benefits of using carrageenan in toothpaste, the wider use of carrageenan has been limited by its high cost compared to other binders, especially carboxymethylcellulose (CMC). Cost is a particular issue in parts of the world where toothpaste, despite its importance for dental hygiene, remains unaffordable. Part of the higher cost of using carrageenan comes from the relatively high cost associated with obtaining the carrageenan raw material from its natural source, seaweed. Another part of the cost comes from the inherent problem of manufacturing toothpaste with binders that build viscosity. For example, heat transfer becomes less efficient as formulations become more viscous requiring greater time for heating and cooling. As formulations become more viscous they do not mix as readily and therefore require greater agitation to achieve appropriate mixing. Also, with high viscosity formulations it is more difficult to obtain consistent and accurate metering at the filling equipment. As a result of the mixing and pumping required for high viscosity formulations, most toothpastes today are prepared by a batch process. Continuous processes, which are theoretically more economical than batch processes, are generally not feasible for toothpastes with carragoenan. However, there have been attempts to design a suitable continuous process (see Catiis et al., U.S. Pat. No. 5,236,696).

Another factor to be considered when using carrageenan is the known thixotropic properties of carrageenan-containing toothpaste. This means that mechanical working of the toothpaste, for example by pumping or mixing, will reduce its viscosity. After the mechanical working is stopped, the toothpaste will regain most of its vicosity over a period of time, but it will not fully return to the viscosity level it had before the mechanical working. To compensate for this loss of viscosity, excess carrageenan must often be employed making its use less cost effective.

One approach to lowering the cost associated with carrageenan has been to seek low cost replacements for all or part of the carrageenan. When used as the sole binder in a toothpaste having a calcium-based polishing agent, carrageenan is typically present in a concentration of about 0.6% to 1.2% by weight of the toothpaste. Carrageenan can sometimes be used in lesser amounts when mixed with natural or synthetic gums and other thickeners such as CMC or xanthan. See, for example, U.S. Pat. No. 4,140,757. In cases where part of the carrageenan is replaced with other binders, oftentimes the total binder concentration must be greater than when carrageenan is used as the sole binder.

In 1982 it was first reported that desired viscosities can be obtained with less carrageenan when a composition is prepared using microwave radiation (U.S. Pat. Nos. 4,353,890; 4,457,908; 4,473,988; and 4,604,280 assigned to Colgate-Palmolive). In this process the dentifrice or cosmetic composition is treated with microwave radiation in such quantity as to raise the temperature to at least the gel-sol temperature of the carrageenan, after which the composition is allowed to quiescently cool. An advantage of this process is that improved viscosities may be obtained with somewhat less carrageenan. The preferred amount of carrageenan in toothpastes made using microwave radiation was reported to be 0.5 to 2.0% by weight, and it was further reported that viscosity increases of almost 90% may be obtained.

In these reported processes for improving the viscosity of carrageenan-containing toothpastes, a critical feature is the use of microwave radiation to raise the temperature of the formulation above the gel sol point of the carrageenan. The use of conventional heating apparatuses to raise the toothpaste temperature above the gel-sol point, as opposed to using microwave heating, has been considered an unsatisfactory means of obtaining improved viscosities (see above-noted patents). Conventional heating has been deemed unacceptable because it may cause losses of moisture and volatile flavor components, changes in flavor compositions and changes in other dentifrice consituents, due to local overheating and aeration of the paste. Additionally it has been believed that production time would be lost due to the slow heating that would be needed to avoid harm to the product.

It has now been found that viscosity enhancements of at least about 100% can be obtained when toothpaste formulations prepared from certain carrageenans are allowed to quiescently cool, for example, in the toothpaste dispenser or container. The significant viscosity enhancements may be obtained by heating the composition in a temperature range that extends well below, as well as near or above, the gel sol point of the carrageenan. The heating may be effected by either conventional or microwave heating to provide toothpastes having desirable physical properties without adversely affecting flavor and other constituents. In accordance with the methods described herein, low levels of the carrageenans, down to about 0.05% based on the weight of the toothpaste, may be used to provide a toothpaste with a desired Cuban viscosity value in the range of about 3 to 12. Compared with previous carrageenan-containing toothpastes, toothpastes of the present invention require considerably less carrageenan and are much easier to process thereby providing considerable cost savings.

SUMMARY OF THE INVENTION

This invention pertains to a process for making toothpaste having low levels of certain carrageenans. The process may be applied to making toothpastes having suitable viscosity using carrageenan levels as low as about 0.05 weight percent. The dentifrice compositions are comprised of one or more of the following carrageenans: iota, modified kappa, or mixtures thereof. According to this invention, viscosity increases of at least about 100% may be obtained when the compositions are allowed to quiescently cool from a temperature at or above about 45° C. Toothpastes prepared using this method are easier to process and require much less carrageenan relative to similar viscosity toothpastes prepared by previous methods. This invention also pertains to certain toothpaste compositions having low levels of carrageenan including those made according to this process.

DETAILED DESCRIPTION OF THE INVENTION

Figure 1:
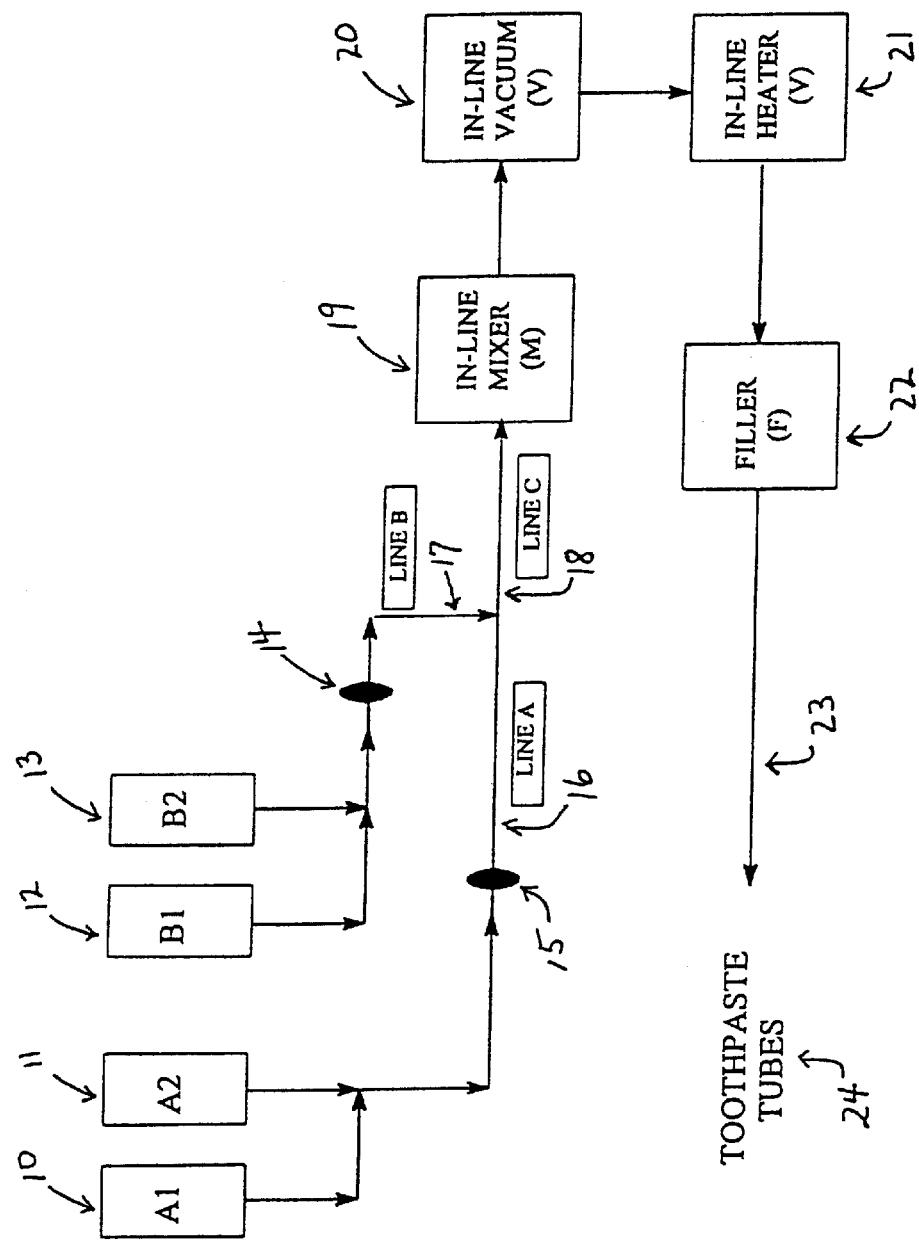
FIG. 1 illustrates a schematic flow of a continuous process that may be used for the manufacture of toothpaste according to this invention.

This invention pertains to a process for making toothpaste having low levels of certain carrageenans. One aspect of this invention pertains to a process for increasing the viscosity of carrageenan-containing dentifrice compositions that comprises allowing the composition to quiescently cool from a temperature at or above about 45° C., wherein the composition comprises a binder, polishing agent, humectant, surfactant and water, the binder comprises carrageenan in an amount of at least about 0.05% by weight of the composition, and the carrageenan is selected from iota,. modified kappa, and mixtures thereof. The viscosity increase may be measured by comparing the viscosity in centipoises of a composition prepared according to the present invention with the viscosity of an identical composition similarly prepared except not allowed to quiescently cool from a temperature above about room temperature. Measuring viscosity increase this way, one may, in accordance with this invention, obtain a viscosity increase of at least about 100% and up to about 900%.

The viscosity increase observed using this invention will depend on the type and amount of carrageenan used and on the temperature from which the composition is allowed to quiescently cool. A preferred viscosity for a toothpaste of this invention will generally be in the range of about 400,000 to 1,400,000 centipoises (cps) when measured at 25° C. Toothpaste viscosity is also commonly measured by the Cuban rack test described below. Suitable Cuban values are in the range of 3 to 12, preferably in the range of 4 to 9. Since Cuban values are typically not recorded for values above 12, a range of 3 to 12 means at least 3 and up to 12. Using the present method, one may obtain an increase in Cuban value of about 1 to 12 and an increase in centipoises of about 160,000 cps to 1,400,000 cps depending on the dentifrice composition and temperature from which it will be quiescently cooled. Unless otherwise noted, viscosities given in centipoises were measured at 25° C. using a Brookfield HAT viscometer.

As a result of the viscosity increase, one advantage of the present process is that very low levels of carrageenan may be used to provide a desired viscosity in the final toothpaste product. Carrageenan concentrations required to provide a suitable viscosity for toothpastes of this invention will be about two to twenty fold less than for prior art carrageenan toothpastes having a similar viscosity. Selecting an appropriate carrageenan concentration will depend in part on whether the polishing agent used in the toothpaste is calcium-based or silica-based. For example, for a calcium-based toothpaste prepared according to this process, the carrageenan level may be as low as about 0.05 to 0.45% by weight of the toothpaste, preferably about 0.075 to about 0.35%, and more preferably about 0.075 to about 0.25%. For a silica-based toothpaste prepared according to this process, the carrageenan level may be as low as about 0.05 to 0.25% by weight of the toothpaste, preferably about 0.075 to about 0.15%.

Viscosity increases are achieved by allowing the dentifrice composition to quiescently cool from a temperature at or above about 45° C. "Quiescent cooling" means that there is little or no mechanical working or disturbance of the gel formed upon cooling. In general, the cooled toothpaste will tolerate some minimal working, such as that which occurs during the squeezing of a toothpaste tube, with little or no loss of viscosity. However, greater mechanical working of the cooled formulation, such as that which occurs as a result of normal pumping or mixing during the manufacturing process, will cause a significant and undesirable loss of viscosity. The term "cooling" as in "quiescent cooling" may refer to either an active or passive cooling process that brings the dentifrice composition to at least around ambient temperature. For example, to quiescently cool one may either refrigerate the dentifrice composition (an active process) or allow it to stand at ambient temperature (a passive process). Unless otherwise specified, dentifrice compositions described herein were allowed to quiescently cool by standing at ambient temperature. A preferred way to quiescently cool toothpaste is to allow it to cool in a toothpaste dispensing tube or in some other container in which the finished toothpaste product will be kept. This avoids mechanical disturbance that may occur while filling the tube or container.

One embodiment of this invention pertains to a process for increasing the viscosity of carrageenan-containing dentifrice compositions that comprises allowing the composition to quiescently cool from a temperature at or above about 55° C. In another embodiment, the composition is allowed to quiescently cool from a temperature at or above about 65° C. In still another embodiment, the composition is allowed to quiescently cool from a temperature at or above about 75° C. At temperatures around or above about 85° C. special processing may be required to avoid degradation or volatilization of toothpaste constituents, especially flavor. Depending on the temperature and composition, it is generally recommended that such high temperature heating be limited to only a few seconds or less and/or performed under a closed system. Therefore, it is generally preferred that the composition not be heated above about 95° C. and preferably not above about 85° C.

When and how the dentifrice compositions are brought to a temperature at or above about 45° C. prior to quiescent cooling will be apparent to one skilled in the art and are not limiting features of this invention. For example, the compositions may be heated using either conventional or microwave heating to a desired temperature at or above about 45° C. prior to quiescent cooling. The term "conventional heating" as used herein refers to heating other than by use of microwave radiation or a microwave generator. Examples of suitable conventional heating apparatuses include, but are not limited to, plate exchangers and double pipe exchangers. In one embodiment of this invention a tube may be filled while the toothpaste is at or near the desired temperature. In another embodiment of the invention, heating of the composition may be effected after the tube has been filled. In this embodiment the toothpaste is heated in the tube, for example by use of an oven. Thus, a toothpaste tube may be filled with a hot formulation and allowed to cool after the tube has been filled. Alternatively, toothpaste in the tube may be heated to a desired temperature so that sequential heating and cooling both occur in the tube.

An important feature of this invention is that the dentifrice compositions may be quiescently cooled from temperatures in a range that extends significantly lower than the gel sol temperature of the carrageenan. For iota and modified kappa carrageenans, the gel sol temperature is typically in the range of about 75° C. to 85° C. Thus, the gel sol temperature is near the upper portion, not the lower limit, of the preferred temperature range of the present method. It is also an advantage of this method that conventional heating as well as microwave heating may be used without adversely effecting the flavor and physical properties of the dentifrice.

The temperatures from which the compositions are to be quiescently cooled are not to be seen as defining upper or lower limits of the process temperatures required for making the compositions. To maximize the increase in viscosity for a given dentifrice composition it is preferred that process temperatures be selected so that the carrageenan is fully hydrated prior to quiescent cooling. For example, it has been found that when process temperatures reach about 75° C. to 85° C. at some stage after the carrageenan has been added, maximum viscosity increases may be obtained even when the compositions are quiescently cooled from a lower temperature. This observed viscosity enhancement is usually slight, about a Cuban value increase of one or less, and is believed to be due to the more complete hydration of carrageenan at the higher temperatures.

The toothpastes of this invention will contain the following general types of ingredients that are typically used in toothpaste: a polishing agent or abrasive, humectant, binder or thickener, surfactant, and water. The humectant and water are also referred to collectively as the vehicle. In addition, agents that provide therapeutic or cosmetic benefits may be optionally added to the toothpaste such as preservatives, fluorides, flavoring agents, sweeteners and tartar control agents. As used herein, the terms "dentifrice" and "toothpaste" are used interchangeably.

The use of carrageenan as a binder or thickener is an important aspect of this invention. The generic term "carrageenan" is applied to dozens of similar polysaccharides found in seaweed. All carrageenans contain repeating galactose units joined by alternating α1→3 and β1→4 glycosidic linkages and are partially sulfated. The types of carrageenans may be distinguished, in part, by their degree and position of sulfation. Iota carrageenan has a repeating unit of D-galactose-4-sulfate-3,6-anhydro-D-galactose-2-sulfate providing a sulfate ester content of about 25 to 34%. Modified kappa carrageenan has a repeating unit of D-galactose-4-sulfate-3,6-anhydro-D-galactose providing a sulfate ester content of about 18 to 25%. "Kappa-iota" carrageenan is a hybrid of kappa and iota carrageenans containing the repeating units of both types in the carrageenan polymer. Lambda carrageenan has a repeating unit of D-galactose-2-sulfate-D-galactose-2,6-disulfate providing a sulfate ester content of about 30 to 40%.

Carrageenan may also be identified by its seaweed source. For example, iota carrageenan may be obtained from *Euchema spinosum* species and kappa carrageenan from *Euchema cottonii*. As discussed above, kappa-iota refers to hybrid types of carrageenan with chemical structures intermediate between those of kappa and iota carrageenan. Kappa-iota carrageenan may also be identified as the carrageenan from *Gigartina radula, Chondrus crispus* and various other species in the Gigartinaceae family from which it may be obtained.

Modification of carrageenan occurs during its processing and extraction from seaweed as a result of alkali treatment at elevated temperatures. A process for alkali modification is described by Stanley in U.S. Pat. No. 3,094,517, which is incorporated herein by reference. Various alkaline materials may be used for the modification including alkaline earth hydroxides such as the hydroxides of calcium, barium, and strontium, sodium carbonate, trisodium phosphate and sodium metaborate. Preferred alkaline materials include calcium hydroxide by itself or as a mixture with sodium hydroxide. The pH during modification is typically above about pH 9, preferably between about pH 9.5 and 13. The temperature for the alkali treatment may range from about 80° C. to about 150° C., with temperatures between 90° C. and about 100° C. being preferable.

The alkali treatment converts a 3-hydroxy-D-galactose-6-sulfate unit into a 3,6-anhydro-D-galactose. At the high pH and temperature, the 3-hydroxyl group is believed to internally displace the 6-sulfate group forming an anhydro ring. Thus, the "modified" form of kappa carrageenan is obtained commercially from "unmodified" kappa. Upon alkali treatment of unmodified kappa at elevated temperatures as described above, displacement of the 6-sulfate occurs to form the anhydro linkage and provide modified kappa carrageenan. As used below, the terms "kappa" and "kappa carrageenan" will refer to one or more members of the kappa family of carrageenans which includes the kappa and kappa-iota carrageenans described above. The term "modified kappa" refers to any such member of the kappa family which has been modified by an alkali treatment such as that described above.

It is not required that the carrageenan be used in purified form. Processed seaweed containing one or more of the carrageenans specified herein may also be used directly. For example, processing of *Euchema cottonii* seaweed by an alkali treatment will modify the kappa carrageenan in the seaweed. Such processed Euchema seaweed is known in the industry as PES and is commercially available. Processed in this manner, Euchema seaweed powder may then be used directly in making the toothpastes of this invention. As used herein, the term "carrageenan" is not limited to carrageenan in purified form and may also refer to carrageenan in processed seaweed, such as processed Euchema seaweed.

A preferred carrageenan for use in this invention is iota carrageenan, modified kappa carrageenan, or a mixture thereof. The term "iota carrageenan" as used herein refers to either modified or unmodified carrageenan, either of which is suitable for the present invention. The amount of carrageenan necessary to provide a desired viscosity will depend, in part, on the type of carrageenan and the amounts and types of other ingredients that are present. As described below, the amount of carrageenan will also depend on the temperature that the dentifrice composition is heated to prior to quiescent cooling.

Carrageenan used in the present invention may be mixed with other natural or synthetic binders or thickeners. Examples of such binders are arboxymethylcellulose (CMC), hydroxyethylcellulose, ydroxypropylcellulose, xanthan gum, locust bean gum, karaya, gum arabic, gum tracanth, and Carbopol. While the amount of carrageenan is an important aspect of this invention, the specific types and the amounts of other ingredients that are employed may be varied in a manner that will be known to those skilled in the art. Very broadly the toothpaste may contain 6 to 60% water, 20 to 60% humectant on a pure basis, 5 to 50% polishing agent, 0.2 to 20% surfactant and 0.1 to 25% other ingredients or adjuvants such as flavoring, sweetening, fluorides, anti-tartars, preservatives, anti-calculus agents and other therapeutic actives compatible with toothpastes.

The usual vehicles of dentifrices, water and one or more humectants, may be used in this invention. The water may be any hygienically clean water such as tap water, well water, and spring water and will often be deionized. Suitable humectants are the known lower straight chain or cyclic polyols of 3 to 6 carbons and mixtures there of. Preferred humectants are glycerol and sorbitol. Sorbitol is readily available as a 70% solution in water. As used herein, the percentages of humectant such as sorbitol refer to the pure humectant in the toothpaste, unless otherwise noted. It is well known to employ glycerol-sorbitol mixtures. Other liquid polyols may also be used, such as propylene glycol, polyethylene glycols, mannitols, xylitols, other sugar alcohols and polyoxyethylene alcohols.

Suitable polishing agents include the known calcium-based and silica-based polishing agents found in toothpaste. These are typically powdered materials having no or very low water solubility and a preferred particle size of about 1 to 40 microns in diameter, more preferably between about 2 to 20 microns in diameter, with normal particle size distributions. All such agents have polishing activity without being objectionably abrasive. Examples of suitable calcium-based polishing agents include dicalcium phosphate, tricalcium phosphate, calcium carbonate, calcium pyrophosphate, calcium silicate, calcium aluminate and mixtures thereof. These polishing agents may be used with other abrasives such as crystalline silica, colloidal silica, complex aluminosilicates, aluminum hydroxide (including alumina trihydrate), magnesium phosphate, magnesium carbonate, bentonite, talc, aluminum oxide, aluminum silicate and silica xerogels. Preferred calcium-based polishing agents are precipitated chalk (calcium carbonate), dicalcium phosphate dihydrate and mixtures thereof.

The amount of carrageenan required will also depend in part on the nature of the polishing agent. In general, slightly more carrageenan will be required when using calcium-based polishing agents. Carrageenan-containing dentifrice compositions having calcium-based polishing agents may be made by a process that comprises allowing the composition to quiescently cool from a temperature at or above about 45° C., wherein the composition comprises a binder, calcium-based polishing agent, humectant, surfactant and water, the binder comprises carrageenan in an amount between about 0.05% and 0.35% by weight of the composition, the carrageenan is selected from iota carrageenan, modified kappa carrageenan, and mixtures thereof, and the composition has a Cuban value in the range of about 3 to 12. In one embodiment of this process, the binder comprises carrageenan and carboxymethylcellulose. Preferably, a composition made by this process will have a Cuban value in the range of 4 to 9.

When dicalcium phosphate (dical) is used as the polishing agent in a carrageenan-containing toothpaste formulation, a preferred concentration of dicalcium phosphate is in the range of about 42 to 55% by weight and more preferably in the range of about 48 to 52%. For the dical formulation, the combined weight percent of humectant and water is preferably in the range of about 40 to 60%, and a preferred humectant system is a glycerol/sorbitol mixture. When calcium carbonate (chalk) is used in a carrageenan-containing toothpaste formulation, a preferred concentration of the chalk is in the range of about 35 to 55% and more preferably about 46 to 52%. For the chalk formulation, the combined weight percent of humectant and water is preferably in the range of about 40 to 60%, and a preferred humectant system is sorbitol. Toothpastes with carrageenan in the range of about 0.05 to 0.35% having the above-mentioned levels of calcium-based polishing agent, humectant and water and a suitable viscosity are new.

This invention also relates to new dentifrice compositions including those made by the present process. New dentifrice compositions comprise a binder, a calcium-based polishing agent, humectant, surfactant and water, wherein the binder comprises carrageenan which is present in the range of about 0.05 to 0.35% by weight of the composition, the weight percent of total binder is less than about 0.5%, the weight percent of polishing agent is in the range of about 35 to 55%, the combined weight percent of humectant and water is in the range of about 40 to 60%, the carrageenan is selected from iota carrageenan, modified kappa carrageenan, and mixtures thereof, and wherein the composition has a Cuban value in the range of about 3 to 12. Preferably, the compositions will have a Cuban value in the range of 4 to 9.

When a silica-based polishing agent is used in a carrageenan-containing toothpaste formulation, a preferred concentration of silica is in the range of about 15 to 30 weight percent and the combined weight percent of humectant and water is in the range of about 25 to 70%. New dentifrice compositions having a silica-based polishing agent comprise a binder, a silica-based polishing agent, humectant, surfactant and water, wherein the binder comprises carrageenan which is present in the range of about 0.05 to 0.15% by weight of the composition, the weight percent of total binder is less than about 0.2%, the weight percent of polishing agent is in the range of about 15 to 30%, the combined weight percent of humectant and water is in the range of about 25 to 70%, the carrageenan is selected from iota carrageenan, modified kappa carrageenan, and mixtures thereof, and wherein the composition has a Cuban value in the range of about 3 to 12. Preferably, the compositions will have a Cuban value in the range of 4 to 9.

Such carrageenan-containing toothpastes may be made by a process that comprises allowing the composition to quiescently cool from a temperature at or above about 45° C., wherein the composition comprises a binder, silica-based polishing agent, humectant, surfactant and water, the binder comprises carrageenan in an amount between about 0.05% and 0.15% by weight of the composition, the carrageenan is selected from iota carrageenan, modified kappa carrageenan, and mixtures thereof, and the composition has a Cuban value in the range of about 3 to 12. Preferably, the compositions will have a Cuban value in the range of 4 to 9 The surfactants (detergents) that may be used in the toothpaste of this invention are those commonly used to emulsify or otherwise uniformly disperse toothpaste components. It is generally preferred that the detergent be anionic or nonionic or a mixture thereof. Suitable types of anionic detergents include sodium lauryl sulfate, fatty acid monoglyceride sulfates, fatty alkyl sulfates, higher alkyl aryl sulfonates, higher alkyl sulfoacetates, higher olefin sulfonates, higher aliphatic acylamides of lower aliphatic aminocarboxylic acids, higher alkyl poly-lower alkoxy (of 3 to 100 alkoxy groups) sulfates, and fatty acid soaps. Examples of these anionic detergents include sodium lauryl sulfate, sodium salt of the monoglyceride monosulfates of hydrogentated coconut oil fatty acids, sodium N-lauroyl sarcoside, and sodium cocate. Suitable types of nonionic detergents include chains of lower alkyene oxides such as ethylene oxide and propylene oxide.

Additional materials that are optionally added include flavorings, sweetening agents, anti-tartar agents, enamel hardening agents, tooth whitening agents and antibacterial compounds. Examples of flavoring materials include flavor oils such as spearmint, peppermint, wintergreen, eucalyptus, lemon and lime. When flavor oils are incorporated in the dentifrice composition of the present invention, they are typically present in a concentration of about 0.1 to 2.0% by weight. Preferred sweeteners include saccharin, sorbitol, sodium cyclamate, and xylitol. Other suitable sweeteners include sucrose, lactose, maltose, perillartine, aspartyl phenyl alanine, and the like. When sweetening agents are incorporated in the dentifrice, they are typically present in a concentration of about 0.1 to 2% by weight. Examples of anti-tartar agents are pyrophosphate salts such as dialkali or tetra-alkali metal pyrophosphate salts including $Na_4P_2O_7$, $K_4P_2O_7$, $Na_2K_2P_2O_7$, $Na_2H_2P_2O_7$, $K_2H_2P_2O_7$, long chain polyphosphates such sodium hexametaphosphate and cyclic phosphates such as sodium trimetaphosphate. Anti-tartar agents, when employed in the dentifrice, are typically present in a concentration of about 0.5% to 8.0% by weight. Examples of hardening agents include sodium monofluorophosphate, sodium fluoride and stannous fluoride. A preferred antibacterial is Triclosan (2,2'-trichloro-2-hydroxy-diphenyl ether), which may be present in a concentration ranging from 0.03% to 1%. Other suitable antibacterials include sodium benzoate and methyl and ethyl parasept. Tooth whitening agents that are useful in this invention include calcium peroxide, hydrogen peroxide, urea peroxide, peracetic acid, and sodium percarbonate. The tooth whitening agent may be present in concentrations ranging from about 0.1% to 5%.

Figure 2:
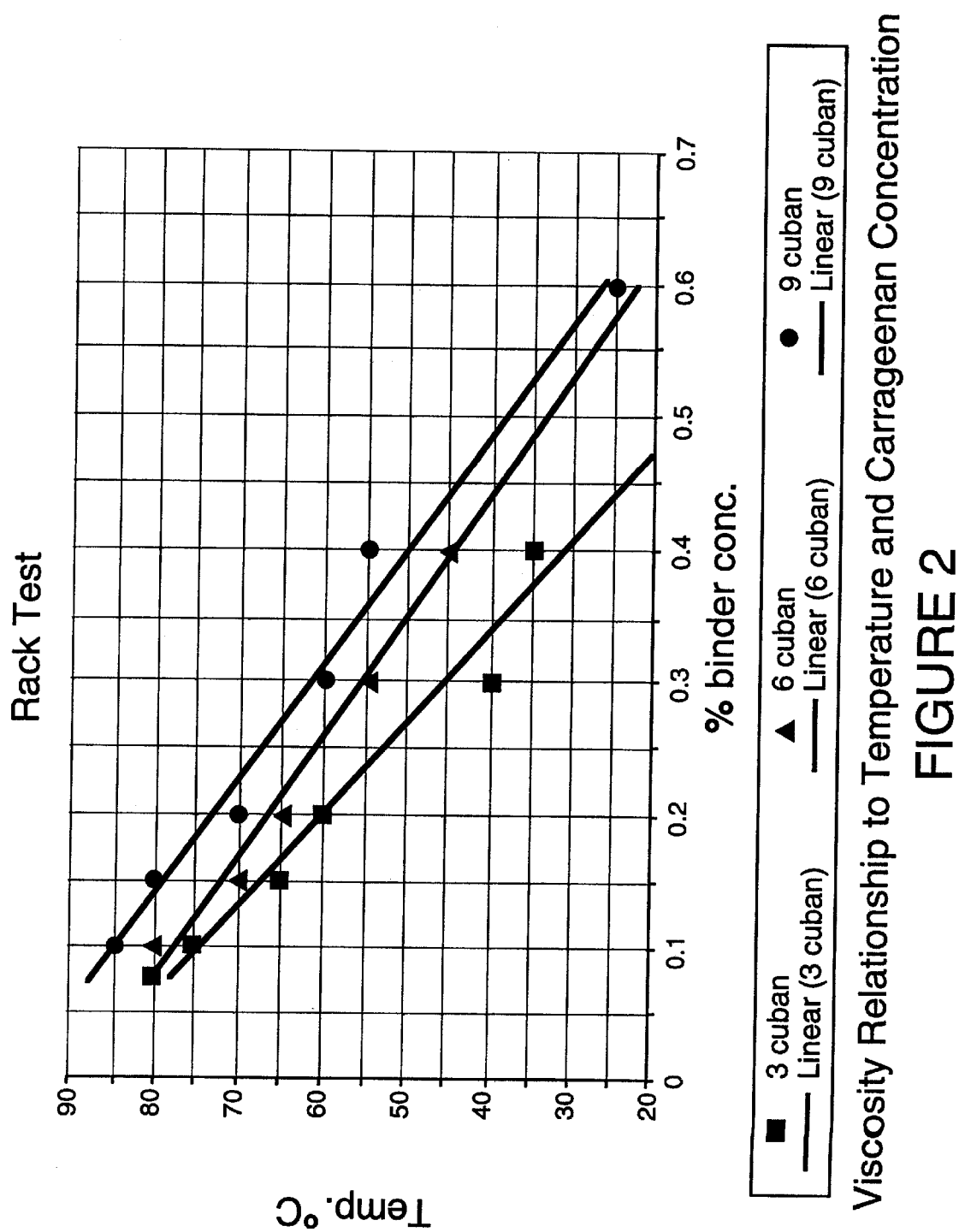
FIG. 2 shows the relationship of viscosity to temperature and to carrageenan concentration.

Depending on the type and amount of carrageenan and the desired viscosity, the composition will be quiescently cooled from a temperature at or above about 45° C. FIG. 2 shows the relationship between carrageenan concentration, temperature and viscosity for a series of modified iota carrageenan formulations which differ only in the amount of carrageenan in an otherwise typical toothpaste formulation using dicalcium phosphate as the polishing agent. The lines approximate the temperature and carrageenan concentration needed to obtain Cuban values of 3, 6 and 9.

As can be seen from FIG. 2, there is an inverse relationship between the amount of carrageenan in the formulation and the temperature required to obtain a suitable viscosity. As the amount of carrageenan is decreased in the formulation, quiescent cooling from a greater temperature is necessary to achieve a suitable viscosity. Thus, when a formulation having 0.1% iota carrageenan is quiescently cooled from about 77° C., a Cuban viscosity level of 6 is obtained in the cooled dentifrice. However, to obtain a Cuban value of 6 in a formulation having 0.3% carrageenan, quiescent cooling from only about 45° C. is sufficient. FIG. 2 also shows that for a given concentration of carrageenan greater viscosity may be obtained by quiescent cooling from a higher temperature.

Either batch or continuous processes may be used to prepare the toothpastes described herein. Such processes are known to those skilled in the art of toothpaste manufacture. The batch processes of this invention are illustrated by, but not limited to, the methods shown below.

Method A

1) A salt mixture containing sodium saccharin, TSPP and MFP were dry blended. The dry blend was dispersed with agitation into a beaker containing the water and the resulting salt solution was heated to about 75° C.

2) In a separate beaker, carrageenan was dispersed into 70% sorbitol and mixed for 5 minutes. The resulting mixture was transferred to a waterbath preheated to a desired temperature and the salt solution prepared in step (1) was added. The resulting binder solution was heated to a desired temperature, between about 75 to 85° C., and held at that temperature for 15 minutes. Water was added as necessary to make up for the loss of water due to evaporation.

3) In an open Ross® Mixer containing dicalcium phosphate dihydrate and flavor oil, the binder solution from step (2) was added. The mixture was wetted out with a rubber spatula, i.e., mixed until a homogenous paste is obtained. The paste was then stirred in a Ross mixer under vacuum for 20 minutes.

4) The vacuum was removed and, after adding 15 g of sodium lauryl sulfate to the paste, the paste was then mixed for 10 minutes under vacuum.

5) The paste was transferred to a beaker and heated to the desired temperature using a water bath.

6) The heated paste was poured into a jar or tube and stored.

Method B is similar to Method A except that the carrageenan and sodium benzoate are dry blended as part of the salt mixture. After the salt mixture was dispersed into the 70% sorbitol solution the steps of Method A were followed.

Method C follows the steps of Method B except that calcium carbonate (chalk) was used in place of dicalcium phosphate dihydrate.

Method D

1) Carrageenan was dispersed in glycerin and mixed for 5 minutes at room temperature.

2) To the mixture from step (1) were added 70% sorbitol and water, and the resulting binder solution was mixed for 10 minutes at room temperature.

3) A dry bend was prepared from sodium saccharin, TSPP, MFP, and titanium dioxide. The dry blend was dispersed into the binder solution from step (2) and the resulting solution was mixed for 2 minutes at room temperature.

4) The solution from step (3) was heated to a desired temperature using a water bath and held at that temperature for 15 minutes.

5) In an open Ross® Mixer containing silica, the binder solution from step (4) was added. The mixture was wetted out with a rubber spatula, i.e., mixed until a homogenous paste is obtained. The paste was then stirred under vacuum for 20 minutes.

6) The vacuum was removed and, after adding flavor oil to the paste, the paste was then mixed for 5 minutes under vacuum.

7) The vacuum was removed and, after adding sodium lauryl sulfate to the paste, the paste was then mixed for 15 minutes under vacuum.

8) The paste was transferred to a beaker and heated with agitation to a desired temperature for 15 minutes using a water bath.

9) The heated paste was poured into a jar or tube which was then stored.

Table 1 shows representative formulations that were prepaed according to the above methods for a batch process.

TABLE 1

Representative Formulations Prepared by Batch Process

|  | Weight % Methods | | | |
| --- | --- | --- | --- | --- |
|  | A | B | C | D |
| Sodium Saccharin | 0.21 | 0.20 | 0.21 | 0.22 |
| TSPP | 0.26 | 0.25 | — | 0.66 |
| Sodium monofluorophosphate | 0.78 | 0.75 | — | 0.27 |
| Titanium dioxide | — | — | — | 0.55 |
| Sodium Benzoate | — | 0.50 | 0.52 | — |
| Carrageenan | 0.21 | 0.20 | 0.21 | 0.22 |
| Sorbitol (70%) | 22.56 | 21.82 | 22.77 | 28.81 |
| Glycerin | — | — | — | 16.62 |
| Dicalcium phosphate | 53.1 | 51.4 | — | — |
| Calcium Carbonate | — | — | 50.1 | — |
| Flavor Oil | 0.82 | 0.79 | 0.83 | 1.11 |
| SLS | 1.54 | 1.49 | 2.07 | 2.22 |
| Silica | — | — | — | 24.38 |
| Water | 20.51 | 22.62 | 23.29 | 24.93 |

An example of a continuous process that is suitable for the method of the present invention is described in U.S. Pat. No. 5,236,696 (Catiis et al.) which is incorporated herein by reference. A similar continuous process is shown in FIG. 1 which illustrates how this process may be performed. Referring to FIG. 1, the A1 tank 10 is charged with carrageenan and glycerine which is mixed at ambient temperature for about 10 minutes. To the B1 tank 12 charged with water heated to about 70° C., sorbitol heated to about 55° C. is added with mixing. To the mixture in the B1 tank 12, sodium monofluorophosphate, sodium saccharin and sodium lauryl sulfate are added and the mixing is continued for 5–10 minutes at about 50 to 55° C. Dicalcium phosphate is added to tank 12 at a temperature of about 50° C. To tank 10, flavor is added with mixing followed by the addition of sodium lauroyl saccosinate at a temperature of about 49° C. and mixing is continued for about 15 to 20 minutes. At this point, tanks 10 and 12 each contain low viscosity slurries.

The slurry from tank 10 is pumped down the A line 16 by pump 15, and the slurry from tank 12 is pumped down the B line 17 by pump 14. The two slurries come together in the C line 18 and are then mixed in an in-line mixer 19. From the in-line mixer 19, the mixed slurry goes through a vacuum device 20 where the mixture is dearated using a vacuum down to about 710 mm. The mixture is then fed into an in-line heater 21 to raise the mixture temperate to the desired temperature. From the heater 21, the toothpaste goes directly to a filling machine 22 and into the final containers 24.

During the above process, similar slurries are prepared in tanks 11 and 13 as described for tanks 10 and 12, respectively. The slurries from the pairs of tanks 10/12 and 11/13 are similarly processed in a sequential manner to permit continuous operation.

As mentioned above, the toothpastes of this invention have low carrageenan levels relative to prior art carrageenan-based toothpastes. By reducing the level of carrageenan required to make a toothpaste, one may achieve a corresponding reduction in in-process viscosity. The in-process viscosity is the viscosity of the toothpaste during its preparation before it is delivered to the toothpaste tube or container in which it is stored. Table 2 below shows a comparison of in-process viscosities for formulations having 0.15% 60% iota carrageenan that were made according to Method A above. The viscosities were measured using a Brookfield LVF viscometer.

TABLE 2

Comparison of In-Process Viscosity for 0.15 and 0.60% Iota Carrageenan

| | Process Steps | Viscosity (cps) | |
| --- | --- | --- | --- |
| Step # | Description | 0.15% | 0.60% |
| 1 | sorbitol solution @ 25° C. | 125 | 125 |
| 2 | #1 + Binder @ 25° C. | 700 | 34,500 |
| 3 | #2 + salt solution @ 25° C. | 15 | 60 |
| 4 | #3 + dical + flavor oil @ 25° C. | 17,600 | 170,000 |
| 5 | #4 + SLS @ 25° C. | 8200 | 110,000 |
| 6 | #5 @ 40° C. | 6400 | 120,000 |
| 7 | #5 @ 60° C. | 5000 | 165,000 |
| 8 | #5 @ 80° C. | 4600 | 180,000 |

According to the present invention, one may prepare a toothpaste having a Cuban value of 3 to 12, where the toothpaste comprises carrageen, humectant, water and a calcium-based polishing agent, by a process where the in-process viscosity never exceeds about 18,000 cps. As Table 2 shows, the reduction in. in-process viscosity during the toothpaste manufacture can be very significant when the level of carrageenan is reduced. In step #8 the difference between 0.15% and 0.60% carrageenan with regard to in-process viscosity is almost 40 fold. At the higher carrageenan level it is noted that the viscosity actually increases as the temperature increases (steps #6 to 8). This is believed to be due to incomplete dissolution of the carrageenan at 40° and 60° C. and improved dissolution as the temperature is increased.

There are several advantages to processing lower viscosity formulations during toothpaste manufacture. As compared to higher viscosity formulations, low viscosity formulations (1) flow more readily during the manufacturing process and therefore require smaller pumps that in turn require less power to operate, (2) allow for more efficient heat transfer since the less viscous formulations require lesser time for heating and cooling, and (3) provide more consistent and accurate metering at the filling equipment. As a result of these advantages, the present method is well-suited for continuous process manufacturing such as described above.

Testing and Results

Viscosity comparisons were made by measuring Cuban values for all samples as well as Brookfield viscosity measurements for selected samples. Cuban test values are directly related to the viscosity of the toothpaste. In the Cuban test (also termed the "Rack" test), the paste is squeezed from a tube through a fixed orifice across a grid of parallel rods, increasingly spaced apart. The test results are expressed as the greatest space number (numbers are from 1–12) which represents the longest distance between rods that support the dentrifice ribbon without having it break. The rack is about 300 millimeters (mm) long and about 100 mm wide. The stainless steel rods are spaced at increasing distances apart starting at 3 mm between rods 1 and 2 (space number 1) and the distance between rods increases by 3 mm from rod to rod. Thus the distance between rods 2 and 3 is 6 mm, and the distance between the twelfth and thirteenth rod (space number 12) is 39 mm. Ratings of 1–2 and 9–12 are not acceptable, 3 and 8 are acceptable, 4–7 are good.

In performing the Cuban test, the following procedure is followed. (1) A nozzle is fixed to a toothpaste tube filled with a toothpaste to be tested. (2) The tube filled with test toothpaste and having the nozzle attached is held at an angle of 45° to the rack device. Pressure is applied at the bottom of the tube and a uniform ribbon of paste is squeezed from the tube. While the ribbon of paste is being extruded from the tube the tube is moved across the rack in a straight line. The time to stretch the ribbon of paste over the rack is usually about two to four seconds. If the ribbon breaks before the entire rack is traversed, the procedure is repeated. (3) The ribbon is allowed to stand for 30 seconds. At that time, the point at which the ribbon breaks is recorded as the rack rating or Cuban value. (4) The test is performed five times and the average reading is recorded, rounding off to the nearest complete figure.

Stability tests were conducted by filling tubes with the sample paste. The tubes were capped and stored flat for 12 weeks at room temperature and at 50° C. After the 12 week exposure, a toothpaste ribbon of about 5 cm length was squeezed from the tube. The tube was then slit open and the ribbon and contents were evaluated for flavor oil and phase separation (syneresis). The separation of the flavoring and water phase at the tip of the toothpaste tube may be noted as "wet cap". Flavor separation was rated as 0=none, 1=slight, 2=moderate and 3=severe. Stability was rated as "not ok", "ok", and "good". To be rated "not ok," the sample readily exhibited some undesirable properties such as flavor separation, syneresis, being very hard in the tube, or having unacceptable Cuban values. To be rated "ok," the sample did not separate but could be somewhat grainy and lacking in good sheen. To be rated "good," the sample exhibited no separation of any sort and the sample was superior in subtle details such as fine texture or not grainy and had superior sheen or gloss.

Comparisons were made among a number of toothpaste formulations prepared as described herein with varying amounts of different carrageenans and at different temperatures. The formulations were then evaluated for viscosity, physical stability and, in selected cases, flavor retention.

Table 3 shows representative formulations of iota carrageenan prepared by Method A described above. The temperatures correspond to the maximum temperature of the formulation prior to quiescent cooling. The results in Table 3 are also graphically depicted in FIG. 2.

Formulations of modified kappa carrageenan were also prepared by Method A described above. For a given Cuban value, modified kappa carrageenan was found to require somewhat greater temperatures or amounts of carrageenan relative to iota carrageenan. However, as compared to prior art methods that employ about 0.6% to 1.2% carrageenan, modified kappa carrageenan may be used according to the present invention at significantly lower levels.

TABLE 4

Hot and Cold Fill Comparisons for Different Binders

| No. | Binder Type[a] | (% conc.) | Method (° C.) | Cuban Ratings[b] Cold Fill | Hot Fill | Oven Fill |
|---|---|---|---|---|---|---|
| 1 | Iota | 0.125 | A (80) | 2 | 7 | — |
| 2 | Iota | 0.15 | A (75) | 2 | 9 | — |
| 3 | Iota | 0.15 | A (80) | 2 | ≧12 | 11 |
| 4 | Iota | 0.15 | A (85) | 1 | ≧12 | ≧12 |
| 5 | Iota | 0.6 | A (75) | 7 | ≧12 | ≧12 |
| 6 | Iota | 0.6 | A (80) | 8 | ≧12 | ≧12 |
| 7 | Iota | 0.6 | A (85) | 8 | ≧12 | ≧12 |
| 8 | Iota | 0.2 | D (85) | 0 | ≧12 | — |
| 9 | Iota | 0.6 | C (80) | 3 | ≧12 | — |
| 10 | Iota | 0.3 | D (80) | 1 | 7 | — |
| 11 | mod. K | 0.3 | A (75) | 3 | ≧12 | ≧12 |
| 12 | mod. K | 0.3 | A (85) | 3 | ≧12 | ≧12 |
| 13 | mod. K | 0.3 | C (80) | 1 | 9 | — |
| 14 | mod. K | 0.3 | D (80) | 1 | 4 | — |
| 15 | unmd. K | 0.15 | A (80) | 1 | 0 | 0 |
| 16 | unmd. K | 0.6 | A (80) | 6 | 5 | 5 |
| 17 | unmd. K/L | 0.15 | A (75) | 1 | 1 | 0 |
| 18 | unmd. K/L | 0.15 | A (85) | 1 | 0 | 1 |
| 19 | unmd. K/L | 0.6 | A (80) | 7 | 7 | 7 |
| 20 | unmd. K/L | 0.6 | A (85) | 8 | 6 | 7 |
| 21 | Kappa-2 | 0.6 | A (80) | 4 | 12 | — |
| 22 | Xanthan | 0.8 | A (75) | 7 | 6 | 5 |
| 23 | Xanthan | 0.8 | A (85) | 6 | 5 | 6 |
| 24 | CMC | 0.8 | A (80) | 7 | — | 7 |

[a]Iota refers to modified iota carrageenan; unmd. K/L refers to unmodified kappa and lambda carrageenans, mod. K refers to modified kappa carrageenan; unmd. K refers to unmodified kappa carrageenan; Kappa-2 refers to hybrid kappa-iota carrageenan; CMC refers to carboxymethylcellulose
[b]Cuban ratings were measured at 25° C.

Table 4 shows comparisons between the use of different types of carrageenan and other binders. The methods shown in the table correspond to those methods described above for a batch process. The temperatures in parentheses indicate the maximum temperatures at which the formulations were heated before being allowed to quiescently cool. Cuban ratings are shown for (a) "cold fill" formulations where the toothpaste containers were filled without quiescent cooling; (b) "hot fill" formulations where the tube or container was

TABLE 3

Temperature and Viscosity Values for Iota Carrageenan Formulations

| Temp. (° C.) | % Iota Carrageenan/Cuban Values | | | | | | |
|---|---|---|---|---|---|---|---|
| | 0.05% | 0.075% | 0.10% | 0.15% | 0.20% | 0.30% | 0.04% |
| 35 | — | — | — | 1 | 1 | 3 | 4 |
| 40 | — | — | — | 1 | 1 | 3 | 5 |
| 45 | — | — | — | 1 | 1 | 4 | 6 |
| 50 | — | — | — | 1 | 2 | 4 | 7 |
| 55 | 0 | — | 0 | 1 | 2 | 6 | 8 |
| 60 | 0 | — | 1 | 2 | 4 | 9 | — |
| 65 | 0 | — | 1 | 5 | 6 | 11 | — |
| 70 | 0 | — | 2 | 7 | 10 | >12 | — |
| 75 | 0 | 2 | 3 | 11 | >12 | >12 | >12 |
| 80 | 1 | 3 | 6 | 11 | >12 | >12 | >12 |
| 85 | 1 | 4 | 9 | — | — | — | — |
| 90 | 1 | 4 | 11 | — | — | — | — | filled while the formulation was hot (at the temperature indicated) and then allowed to quiescently cool; and (c) "oven fill" formulations where the toothpastes were heated in the tube or container prior to quiescent cooling. Of the binders tested, the Cuban ratings or viscosity differences in the cold fill versus hot fill methods were most significant for formulations containing iota and modified kappa and kappa-2 carrageenans. For these types of carrageenans, the methods of this invention provide viscosity increases in excess of 100% as compared to corresponding cold fill methods.

Selected samples were measured for flavor separation and stablility. With few exceptions, samples prepared according to the present process having a Cuban value of 4 to 9 exhibited a flavor separation rating of 0 or 1 and a stability rating of OK or good.

What is claimed is:

1. A process for increasing the viscosity of a carrageenan-containing dentifrice composition, the process comprising:
   heating the dentifrice composition to a temperature between 45° C. and 95° C.;
   allowing the composition to quiescently cool from a temperature at or above 45° C.;
   wherein:
   the composition comprises a binder, a polishing agent, a humectant, a surfactant, and water;
   the composition comprises 0.05% to 0.45% by weight carrageenan;
   the carrageenan is selected from the group consisting of iota carrageenan, modified kappa carrageenan, and mixtures thereof;
   the viscosity increase is about 100% to 900%; and
   after the increase in viscosity the composition has a room temperature viscosity of about 160,000 cp to about 1,400,000 cp.

2. The process of claim 1 wherein the composition is allowed to quiescently cool from a temperature at or above 55° C.

3. The process of claim 1 wherein the composition is allowed to quiescently cool from a temperature at or above 65° C.

4. The process of claim 1 wherein the composition is allowed to quiescently cool from a temperature at or above 75° C.

5. A process for increasing the viscosity of a carrageenan-containing dentifrice composition, the process comprising:
   heating the dentifrice composition to a temperature between 45° C. and 95° C.;
   allowing the composition to quiescently cool from a temperature at or above 45° C.;
   wherein:
   the composition comprises a binder, a polishing agent, a humectant, a surfactant, and water;
   the composition comprises 0.05% to 0.45% by weight carrageenan;
   the carrageenan is selected from the group consisting of iota carrageenan, modified kappa carrageenan, and mixtures thereof;
   the viscosity increase is about 100to 900%; and
   after the increase in viscosity the composition has a Cuban value in the range of 3 to 12 after the increase in viscosity.

6. The process of claim 5 in which the Cuban value is in the range of 4 to 9.

7. The process of claim 6 in which:
   the polishing agent is a calcium-based polishing agent;
   the carrageenan comprises 0.05% to 0.35% by weight of the composition;
   the binder comprises less than about 0.5% of the composition;
   the polishing agent comprises about 35 to 55% by weight of the composition;
   the humectant and water comprises about 40 to 60% by weight of the composition.

8. The process of claim 6 in which:
   the polishing agent is a silica-based polishing agent;
   the carrageenan comprises 0.05% to 0.15% by weight of the composition;
   the binder comprises less than about 0.2% of the composition;
   the polishing agent comprises about 15 to 30% by weight of the composition;
   the humectant and water comprises about 25 to 70% by weight of the composition.

9. The process of any of claims 5, 6, 7, and 8 in which the composition is allowed to quiescently cool from a temperature at or above 65° C.

10. The process of claim 9 in which the carrageenan is iota carrageenan.

11. The process of any of claims 5, 6, 7, and 8 in which the composition is allowed to quiescently cool from a temperature at or above 75° C.

12. The process of claim 11 in which the carrageenan is iota carrageenan.

13. The process of any of claims 1, 2, 3, and 4 wherein the carrageenan comprises about 0.05 to about 0.35, by weight of the composition.

14. The process of any of claims 1, 2, 3 and 4 wherein the carrageenan comprises about 0.05 to about 0.25% by weight of the composition.

15. The process of claim 1 wherein the binder additionally comprises and carboxymethylcellulose.

16. The process of any of claims 1, 2, 3, and 4 in which the heating step is carried out in a toothpaste tube or dispenser.

17. The process of claim 13 wherein the binder additionally comprises carboxymethylcellulose.

18. The process of claim 7 in which the in-process viscosity never exceeds about 18,000 cps.

19. The process of any of claims 1, 2, 3, and 4 in which heating is by microwave heating.

20. The process of any of claims 1, 2, 3, and 4 wherein the binder comprises less than 0.5% weight percent of the composition, and the carrageenan comprises about 0.05% to 0.35% weight percent of the composition.

21. The process of any of claims 1, 2, 3, and 4 wherein the binder comprises less than 0.2% weight percent of the composition, and the carrageenan comprises about 0.05% to 0.15% weight percent of the composition.

22. The process of any of claims 5, 6, 7, 8 further comprising the step of heating the dentifrice composition in a toothpaste tube or dispenser before allowing it to quiescently cool.

23. The process of claim 6 in which the binder additionally comprises and carboxymethyl cellulose.

* * * * *